United States Patent [19]
Niewöhner et al.

[11] Patent Number: 5,861,404
[45] Date of Patent: Jan. 19, 1999

[54] 2,9-DISUBSTITUTED PURIN-6-ONES

[75] Inventors: Ulrich Niewöhner, Wermelskirchen; Erwin Bischoff, Wuppertal; Helmuth Schütz, Wuppertal; Elisabeth Perzborn, Wuppertal; Matthias Schramm, Leverkusen, all of Germany

[73] Assignee: Bayer Aktiengesellschaft, Leverkusen, Germany

[21] Appl. No.: 587,321

[22] Filed: Jan. 12, 1996

[30] Foreign Application Priority Data

Jan. 19, 1995 [DE] Germany .................. 195 01482.0

[51] Int. Cl.$^6$ .................. A61K 31/52; C07D 473/30; C07D 233/90
[52] U.S. Cl. ................................... 514/262; 544/265
[58] Field of Search .................. 544/265; 514/262

[56] References Cited

U.S. PATENT DOCUMENTS 4,451,478 5/1984 Simon et al. .................. 544/277

FOREIGN PATENT DOCUMENTS 0178178 4/1986 European Pat. Off. .
9400453 1/1994 WIPO .

OTHER PUBLICATIONS

Y. Ohtsuka, Bulletin of the Chemical Society of Japan, vol. 43, No. 12, pp. 3909–3913, (1970).

A.M. Khairy et al., Egypt. J. Chem., vol. 83, No. 3, pp. 243–253, (1990).

J.L. Kelley, et al., J. Med. Chem., vol. 32, pp. 218–224, (1989).

J.A. Beavo, et al., TIPS, vol. 11, pp. 150–155, (1990).

F.I. Logemann, et al., Chemistry and Industry, (13), pp. 541–542, (1980).

L.R. Krepski, et al., Synthesis, pp. 301–303, (1986).

R.A. Kenley, et al., Journal of Pharmaceutical Sciences, vol. 74, No. 10, pp. 1082–1085, (1985).

A. Parkin, et al., J. Heterocyclic Chem., vol. 19, No. 1, pp. 33–40, (1982).

I.M. Obcharoba, et al., Khim. Form Zh., vol. 8, No. 4, pp. 26–28, (1974).

*Primary Examiner*—Mark L. Berch
*Attorney, Agent, or Firm*—Sprung Kramer Schaefer & Briscoe

[57] ABSTRACT

2,9-Disubstituted purin-6-ones are prepared by acylating correspondingly substituted aminoimidazoles in a first step and then cyclizing the product to the purine. The new 2,9-disubstituted purin-6-ones can be employed as active compounds in medicaments, in particular for the treatment of inflammations, thromboembolic and cardiovascular diseases and diseases of the urogenital system.

12 Claims, No Drawings

2,9-DISUBSTITUTED PURIN-6-ONES

The present invention relates to 2,9-disubstituted purin-6-ones, a process for their preparation and their use in medicaments, in particular for the treatment of inflammations, thromboembolic and cardiovascular diseases and diseases of the urogenital system.

Some 2-phenyl-substituted 6H-purin-6-ones are known from the publications J. Pharm. Sci., 74 (10), 1082–85, 1985 and J. Hetero. Chem. 19 (1), 33–40, 1982.

1H-9-Methyl-substituted purines and oxazolopyrmidines have furthermore been described [in this context cf. Khim.-Farm. Zh. 8(4), 26–8, 1974 and Bull. Chem. Soc. Jap. 43 (12), 3509–13 (1970)].

9-Substituted hypoxanthines are furthermore known from JP 47 021 434.

Moreover, purine derivatives having a regulating action on plant growth and 2-substituted 9-(4methylbenzyl)-9H-purines having an anti-rhinovirus action are known [cf. Egypt. J. Chem., Vol. Data 1990, 33 (3), 243–53, 1991 and J. Med. Chem. 32 (1), 218–24, 1989].

Phosphodiesterases (PDEs) play an essential role in the regulation of the intracellular cGMP and cAMP level. Of the phosphodiesterase isoenzyme groups PDE I to PDE V described to date [nomenclature according to Beavo and Reifsnyder (cf. Beavo, J. A. and Reifsnyder, D.H.: Trends in Pharmacol. Sci 11, 150–155 (1990))], the Ca-calmodulin-activated PDE I, the cGMP-stimulatable PDE II and the cGMP-specific PDE V are essentially responsible for the metabolism of cGMP. Because of the different distribution of these cGMP-metabolizing PDEs in tissue, selective inhibitors should raise the cGMP level in the corresponding tissue depending on the tissue distribution of the corresponding isoenzyme. This can lead to a specific antiaggregatory, antispastic, vasodilating, antiarrhythmic and/or antiinflammatory action.

The present invention thus relates to 2,9-disubstituted purin-6-ones of the general formula (I)

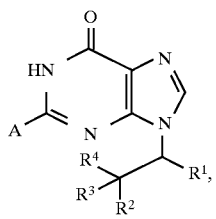

in which $R^1$ represents straight-chain or branched alkyl having 2 to 10 carbon atoms, which is optionally substituted by phenyl, which in turn can be substituted by halogen, nitro, cyano or by straight-chain or branched alkyl having up to 6 carbon atoms, $R^2$ represents hydrogen, hydroxyl or azido, or represents straight-chain or branched alkyl having up to 6 carbon atoms, or represents a group of the formula $-O-SO_2^5$, wherein $R^5$ denotes straight-chain or branched alkyl having up to 4 carbon atoms or phenyl, $R^3$ represents hydrogen, or $R^2$ and $R^3$ together form the radical of the formula =O, $R^4$ represents hydrogen, or represents straight-chain or branched alkyl having up to 4 carbon atoms, and A represents a radical of the formula or

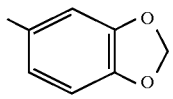

represents straight-chain or branched alkyl having up to 20 carbon atomns, or represents cycloalkyl having 3 to 7 carbon ators, or represents phenyl, which are optionally substituted up to 2 times in an identical or different manner by halogen, carboxyl, trifluoromethyl, nitro, cyano or by straight-chain or branched alkyl, alkoxycarbonyl or alkoxy having in each case up to 5 carbon atoms, which in their turn can be substituted by phenyl, and/or the rings are optionally substituted by phenyl, which in turn can be substituted by straight-chain or branched alkoxy having up to 5 carbon atoms, and tautomers and salts thereof The substances according to the invention can also be in the forn of salts. Physiologically acceptable salts are preferred in the context of the invention.

Physiologically acceptable salts can be salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds of the general formula (I) according to the invention can occur in various stereochemical forms which either behave as mirror images (enantiomers) or do not behave as mirror images (diastereomers). The invention relates both to the antipodes and to the racemic forms, as well as the diastereomer mixtures. The racemic forms, like the diastereomers, can be separated into the stereoisomerically uniform constituents in a known manner.

Preferred compounds are those of the general formula (I) in which $R^1$ represents straight-chain or branched alkyl having 2 to 8 carbon atoms, which is optionally substituted by phenyl, which in turn can be substituted by fluorine, chlorine, bromine, nitro, cyano or by straight-chain or branched alkyl having up to 4 carbon atoms, $R^2$ represents hydrogen, hydroxyl or azido, or represents straight-chain or branched alkyl having up to 4 carbon atoms or a group of the formula $-O-SO_2R^5$, wherein $R^5$ denotes straight-chain or branched alkyl having up to 3 carbon atoms or phenyl, $R^3$ represents hydrogen, or $R^2$ and $R^3$ together form the radical of the formula =O, $R^4$ represents hydrogen, or represents straight-chain or branched alkyl having up to 3 carbon atoms, and A represents a radical of the formula

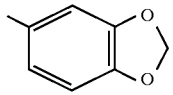

represents straight-chain or branched alkyl having up to 19 carbon atoms, or represents cyclopropyl, cyclopentyl, cyclohexyl or cycloheptyl, or represents phenyl, which are optionally substituted up to 2 times in an identical or different manner by fluorine, chlorine, bromine, carboxyl, nitro, hydroxyl or by straight-chain or branched alkyl, alkoxycarbonyl or alkoxy having in each case up to 4 carbon atoms, which in their turn can be substituted by phenyl, and/or the rings are optionally substituted by phenyl, which in turn can be substituted by straight-chain or branched alkoxy having up to 4 carbon atoms,
and tautomers and salts thereof.

Particularly preferred compounds are those of the general formula (I)
in which
$R^1$ represents straight-chain or branched alkyl having 2 to 7 carbon atoms, which is optionally substituted by phenyl, which in turn can be substituted by fluorine, chlorine, bromine, nitro, cyano or by straight-chain or branched allyl having up to 3 carbon atoms,
$R^2$ represents hydrogen, hydroxyl or azido, or represents straight-chain or branched alkyl having up to 3 carbon atoms or a group of the formula —$OSO_2R^5$,
wherein
$R^5$ denotes straight-chain or branched alkyl having up to 3 carbon atoms or phenyl, $R^3$ represents hydrogen,
or
$R^2$ and $R^3$ together form the radical of the formula =O,
$R^4$ represents hydrogen, or represents staight-chain or branched alkyl having up to 3 carbon atoms, and
A represents a radical of the formula

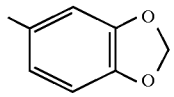

represents straight-chain or branched alkyl having up to 18 carbon atoms, or represents cyclopropyl, cyclopentyl, cyclohexyl, cycloheptyl or phenyl, which are optionally substituted up to 2 times in an identical or different manner by fluorine, chlorine, bromine, carboxyl, nitro, hydroxyl or by straight-chain or branched alkyl, alkoxycarbonyl or alkoxy having in each case up to 3 carbon atoms, which in their turn can be substituted by phenyl, and/or the rings are optionally substituted by phenyl, which in turn can be substituted by straight-chain or branched alkoxy having up to 3 carbon atoms,
and tautomers and salts thereof A process has furthermore been found for the preparation of the compounds of the general formula (I) according to the invention, characterized in that compounds of the general formula (II)

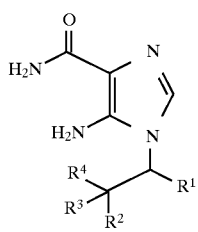

in which
$R^1$, $R^2$, $R^3$ and $R^4$ have the abovementioned meanings, are first converted, by reaction with compounds of the general formula (III)

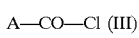

in which

A has the abovementioned meaning,
in inert solvents and in the presence of a base,
into the compounds of the general formula (IV)

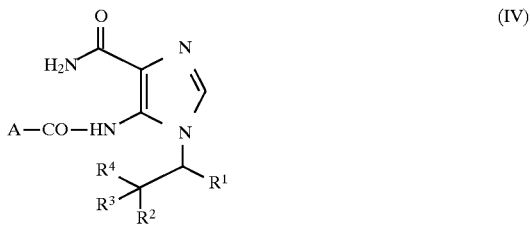

in which
A, $R^1$, $R^2$, $R^3$ and $R^4$ have the abovementioned meaning, these are cyclized in a second step in inert solvents and in the presence of a base,
and the substituents $R^1$, $R^2$, $R^3$ and $R^4$ are introduced or derivatized by acylation, oxidation and/or azide exchange.

The process according to the invention can be illustrated by way of example by the following equation:

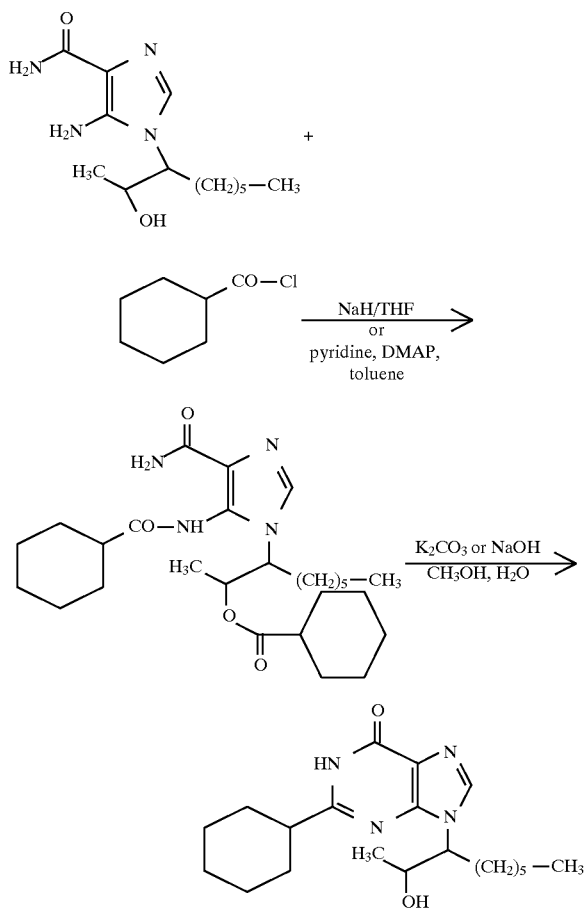

Inert organic solvents which do not change under the reaction conditions are suitable for the first step of the process. These include, preferably, ethers, such as, for example, diethyl ether, dioxane, tetrahydrofuran or glycol mono- or dimethyl ether, halogenated hydrocarbons, such as methylene chloride, chloroform or carbon tetrachloride, dichloroethylene or trichloroethylene, ethyl acetate, toluene, acetonitrile, hexamethylphosphoric acid triamide, pyridine and acetone. It is of course possible to employ mixtures of the solvents. Tetrahydrofuran, toluene or pyridine are particularly preferred.

Suitable bases are in general alkali metal hydrides or alcoholates, such as, for example, sodium hydride or potassium tert-butylate, or cyclic arnines, such as, for example, piperidine, pyridine or dimethylarninopyridine, or $C_1$–$C_4$-alkylamines, such as, for example, triethylamine. Sodium hydride, pyridine or dirnethylaminopyridine are preferred.

The base is in general employed in an amount of 1 mol to 4 mol, preferably 1.2 mol to 3 mol, in each case per mole of the compounds of the general formula (II).

The reaction temperature can in general be varied within a relatively wide range. The reaction is in general carried out in a range from −20° C. to 200° C., preferably from 0° C. to 25° C.

In one variant, the reaction is carried out in pyridine, to which a catalytic amount of DMAP is added. If appropriate, toluene can also be added.

Suitable solvents for the cyclization are the customary organic solvents. These include, preferably, alcohols, such as methanol, ethanol, propanol, isopropanol or butanol, or ethers, such as tetaahydrofirn or dioxane, or dimethylformamide or dimethyl sulphoxide. Alcohols, such as methanol, ethanol, propanol or isopropanol, are particularly preferably used. It is also possible to employ mixures of the solvents mentioned.

Suitable bases for the cyclization are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate, or alkali metal alcoholates, such as sodium -methanolate, sodium ethanolate, potassium methanolate, potassium ethanolate or potassium tert-butanolate. Potassium carbonate and sodium hydroxide are particularly preferred.

In carrying out the cyclization, the base is in general employed in an amount of 2 to 6 mol, preferably 3 to 5 mol, per mole of the compounds of the formula (IV).

The cyclization is in general carried out in a temperature range from 0° C. to 160° C., preferably at the boiling point of the particular solvent.

The cyclization is in general carried out under normal pressure. However, it is also possible to carry out the process under increased pressure or under reduced pressure (for example in a range from 0.5 to 5 bar).

The reaction with alkylsulphonic acid chlorides, starting from the corresponding free hydroxy compounds, is carried out in one of the abovementioned solvents and one of the bases, preferably with methylene chloride and triethylamine, in a temperature range from −20° C. to +20° C., preferably 0° C., under normal pressure.

The azide radical is in general introduced by reaction of the corresponding alkylsulphonyloxy-substituted compounds with sodium azide in one of the abovementioned solvents, preferably dimethylformamide, in a temperature range from 50° C. to +120° C., preferably 100° C., under normal pressure.

The ketones are prepared by known methods (Swern oxidation) starting from the corresponding hydroxy compounds.

The enantiomerically pure compounds are accessible by customary methods, for example by chromatography of the racemic compounds of the general formula (I) on chiral phases.

The compounds of the general formula (III) are known.

The compounds of the general formula (IV) are new in most cases and can be prepared, for example, as described above.

The compounds of the general formula (II) are new in most cases and can be prepared, for example, by a procedure in which 2-amino-2-cyanoacetamide of the formula (V)

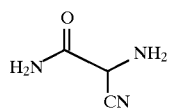

(V)

is reacted with compounds of the general formula (VI)

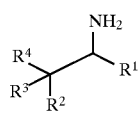

(VI)

in which $R^1$, $R^2$, $R^3$ and $R^4$ have the abovementioned meanings, in inert solvents in the presence of triethyl orthoformate.

Suitable solvents for the individual steps of the processes are the customary organic solvents which do not change under the reaction conditions. These include, preferably, ethers, such as diethyl ether, dioxane, tetrahydrofiran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, dimethylformamide, hexamethylphosphoric acid triamide, acetonitrile, acetone or dimethoxyethane. It is also possible to use mixtures of the solvents mentioned. Acetonitrile is particularly preferred.

The process according to the invention is in general carried out in a temperature range from 0° C. to +180° C., preferably from +30° C. to +150° C.

These process steps according to the invention are in general carried out under normal pressure. However, it is also possible for them to be carried out under increased pressure or under reduced pressure (for example in a range from 0.5 to 5 bar).

The compound of the formula (V) is known [cf. Logemann, G. Shaw, Chemistry and Industry, 1980 (13), 541–542].

The amines of the general formula (VI) are known in some cases or are new, and can then be prepared by known methods [cf L. R. Krepski et al., Synthesis, 1986, 301–303].

The compounds of the general formula (I) according to the invention display an unforeseeable valuable pharmacological action spectrum.

They inhibit either one or more of the cGMP-metabolizing phosphodiesterases (PDE I, PDE II and PDE V). This leads to a differentiated increase in cGMP. An increase in the cGMP level can lead to an antithrombotic, vasodilatory and/or antiarrhythmic action. The selectivity is also determined by the distribution of the isoenzymes in the tissue.

The compounds according to the invention firthermore intensify the action of substances, such as, for example, EDRF (endothelium-derived relaxing factor) and ANP (atrial natriuretic peptide), which increase the cGMP level.

They can therefore be employed in medicaments for the treatment of inflammatory diseases, such as, for example, asthma, inflammatory dermatoses, for the treatment of high blood pressure, stable and unstable angina, peripheral and cardiac vascular diseases and of arrhythmias, for the treatment of thromboembolic diseases and ischaemias, such as myocardial infarction, cerebral stroke, transitory and ischaemic attacks, angina pectoris, peripheral circulatory disturbances, prevention of restenoses, such as after thrombolysis treatments, percutaneous transluminal angioplasties (PTA) and bypass, percutaneous translumninal coronary angioplasties (PTCA), bypass, septic shock and diseases of the urogenital system,. such as, for example, prostate hypertrophy, impotence and incontinence.

Activity of the phosphodiesterases (PDEs)

The cGMP-stimulatable PDE II, the cGMP-inhibitable PDE III and the cAMP-specific PDE IV were isolated from either porcine or bovine myocardium. The Ca-calmodulin-stimulatable PDE I was isolated from the porcine aorta or porcine brain. The cGMP-specific PDE V was obtained from the porcine small intestine, porcine aorta and/or human blood platelets. Purification was carried out by anion exchange chromatography over MonoQ Phaacia essentially by the method of M. Hoey and Miles D. Houslay, Biochemical Pharmacology, Vol. 40, 193–202 (1990).

The enzyme activity is determined in a test batch of 100 $\mu$l in 20 mM Tris/HCl buffer of pH 7.5 which comprises 5 mM $MgCl_2$, 0.1 mg/ml of bovine serum albumin and either 800 Bq of $^3$HcAMP or $^3$HcGMP. The final concentration of the corresponding nucleotides is $10^{-6}$ mol/l. The reaction is started by addition of the enzyme and the amount of enzyme is chosen such that about 50% of the substrate is reacted during the incubation time of 30 minutes. To test the cGMP-stimulatable PDE II, $^3$HcAMP is used as the substrate and $10^{-6}$ mol/l of non-labelled cGMP is added to the batch. To test the Ca-calmodulin-dependent PDE I, 1 $\mu$M $CaCl_2$ and 0.1 $\mu$M calmodulin are also added to the reaction batch. The reaction is stopped by addition of 100 $\mu$l of acetonitrile which comprises 1 mnM cAMP and 1 mM AMP. 100 $\mu$l of the reaction batch are separated on the HPLC column and the cleavage products are determined quantitatively "online" with a flow-through scintillation counter. The substance concentration at which the rate of reaction is reduced by 50% is measured.

| Inhibition of the phosphodiesterases in vitro | | | |
|---|---|---|---|
| Example No. | PDE I $IC_{50}$ [$\mu$M] | PDE II $IC_{50}$ [$\mu$M] | PDE V $IC_{50}$ [$\mu$M] |
| 5 | 10 | 3 | 50 |
| 8 | 40 | 2 | |
| 14 | 4 | 0.6 | 0.3 |
| 20 | 1 | 0.4 | 1 |
| 25 | 3 | 0.1 | 10 |

The compounds were investigated for antihypertensive activity on anaesthetized pigs.

The antihypertensive activity was measured after intravenous adminitration to SHR rats.

To determine the cyclic nucleotides, heart and aorta tissue was removed and deep frozen immediately. The samples were powdered under liquid $N_2$ and extracted with 70% ethanol and the content of cGMP and cAMP was determined with commercial radioimmunoassays (Amersham).

The erection-inducing action was measured on anaesthetized rabbits. (C. G. Stief et al. World Journal Urology 1990, pages 233–236).

The substances were administered in dosages of 0.1 to 10 mg/kg either directly into the corpus cavernosum or intraduodenally, rectally, orally, tnansdernally or intravenously.

The new active compounds can be converted in a known manner into the customary formulations, such as tablets, coated tablets, pills, granules, aerosols, syrups, emulsions, suspensions and solutions, using inert, non-toxic, pharmaceutically suitable carriers or solvents. The therapeutically active compound should in each case be present here in a concentration of about 0.5 to 90% by weight of the total mixture, i.e. in amounts which are sufficient to achieve the stated dosage range.

The formulations are prepared, for example, by extending the active compounds with solvents and/or carriers, if appropriate using emulsifying agents and/or dispersing agents, it being possible, for example in the case of the use of water as a diluent, for organic solvents to be used as auxiliary solvents if appropriate.

The formulations are administered in the customary manner, preferably orally, parenterally, transdermally, perlingually or intravenously.

In general, it has proved advantageous in the case of intravenous administration to administer amounts of about 0.01 to 10 mg/kg, preferably about 0.1 to 10 mg/kg, of body weight to achieve effective results.

Nevertheless, it may be necessary to deviate from the amounts mentioned, and in particular as a finction of the body weight or the nature of the administration route, of the behaviour of the individual towards the medicament, of the nature of the formulation thereof and of the time or interval at which administration takes place. Thus, in some cases it may be sufficient to manage with less than the abovementioned minimum amount, while in other cases the upper limit mentioned must be exceeded In the case of administration of relatively large amounts, it may be advisable to divide these into several individual doses over the course of the day.

STARTING COMPUNDS

General woling insltuctions for the synthesis of the 1-substituted 5acylaminoimidazole-4-carboxamides (formula IV)

Method A:

10 mmol of the 1-substituted 5-amino-imidazole-4-carboxamide and 15 mmol (60% strength dispersion in mineral oil) of NaH (or 30 mmol of NaH, if $R^2$ represents a hydroxyl group) are stirred in 50 ml of absolute tetrahydrofuran at 20° C. for 3 hours (sparingly soluble imidazoles are refluxed for up to 3 hours). 10 mmol of acid chloride (or 20 rnmol if a hydroxyl group is present) in 2.5 ml of absolute tetrahydrofaran are added dropwise at 20° C. and the mixture is stirred overnight at room temperature. The solvent is removed on a rotary evaporator in vacuo, the residue is taken up in 50 ml of ethyl acetate and the mixture is shaken with 50 ml of water. The organic phase is separated off and dried with $Na_2SO_4$ and the solvent is evaporated in vacuo. The residue is purified by recrystallization or flash chromatography.

Method B:

10 mmol of the 1-substituted 5-amino-imidazole-4carboxamide are dissolved in 20 ml of dry pyridine. After addition of 50 mg of 4-dimethylamninopyridine DMAP), 11 mmol of acid chloride (or 22 mmol, if $R^2$ represents a hydroxyl group) are added dropwise at 20° C. (solid acid chlorides are dissolved in a little absolute toluene). The mixture is stirred at 20° C for 1 hour, and in some cases heating at 50° C. for 1–2 hours is also necessary (monitoring by TLC). The batch is poured into 100 ml of ice-water and extracted by shaking 3 times with 50 ml of ethyl acetate each time. The combined ethyl acetate phases are washed twice with 1 N HCI and once with saturated NaCl solution, dried over $Na_2SO_4$ and evaporated in vacuo. The residue is purified by flash chromatography or recrystallization.

The 1-substituted 5-acylamino-imidazole4-carboxarnides listed in Table I are prepared by these two processes:

TABLE I

[Structure: core imidazole-carboxamide with A-C(O)-NH- substituent and N-CH(R¹)-CH(R²)(R⁴) chain]

| Example No. | A | R⁴ | R² | R¹ | Method | Yield (% of theory) | R_f*) |
|---|---|---|---|---|---|---|---|
| I | —CH₃ | CH₃ | —O-C(O)-CH₃ | n-hexyl | A | 33 | 0.40 |
| II | —C(CH₃)₃ | CH₃ | —O-C(O)-C(CH₃)₃ | n-hexyl | A | 28 | 0.45 |
| III | -n-C₁₇H₃₅ | CH₃ | —O-C(O)-C₁₇H₃₅ | n-hexyl | B | 50 | 0.48 |
| IV | —C₆H₅ | CH₃ | —O-C(O)-C₆H₅ | n-hexyl | A | 19 | 0.39 |
| V | -4-Cl—C₆H₅ | CH₃ | —O-C(O)-(4-Cl-C₆H₄) | n-hexyl | A | 15 | 0.40 |
| VI | cyclohexyl-CH< | CH₃ | —O-C(O)-cyclohexyl | n-hexyl | B | 52 | 0.43 |
| VII | cyclohexyl-CH< | CH₃ | H | n-hexyl | A | 16 | 0.38 |
| VIII | cyclohexyl-CH< | CH₃ | —O-C(O)-cyclohexyl | —CH₂CH₂CH₂—C₆H₅ | B | 45 | 0.41 |
| IX | cyclohexyl | H | H | —CH₂CH₂CH₂—C₆H₅ | B | 41 | |
| X | C₆H₅ | H | H | —CH₂CH₂CH₂—C₆H₅ | B | 27.9 | |
| XI | 4-Cl-C₆H₄ | H | H | —CH₂CH₂CH₂—C₆H₅ | B | 17.3 | |

TABLE I-continued

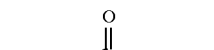

| Example No. | A | R⁴ | R² | R¹ | Method | Yield (% of theory) | R_f*) |
|---|---|---|---|---|---|---|---|
| XII | 4-Me-phenyl | H | H | —CH₂CH₂CH₂-phenyl | B | 37.9 | |
| XIII | isopropyl | H | H | —CH₂CH₂CH₂-phenyl | B | 29.2 | |
| XIV | cyclopropyl | H | H | —CH₂CH₂CH₂-phenyl | B | 38.7 | |
| XV | 4-NO₂-phenyl | H | H | —CH₂CH₂CH₂-phenyl | B | 15.7 | |
| XVI | 4-OMe-phenyl | H | H | —CH₂CH₂CH₂-phenyl | B | 18.3 | |
| XVII | 3-OMe-phenyl | H | H | —CH₂CH₂CH₂-phenyl | B | 44.7 | |
| XVIII | 2-MeO-phenyl | H | H | —CH₂CH₂CH₂-phenyl | B | | |
| XIX | cyclopentyl | H | H | —CH₂CH₂CH₂-phenyl | B | 48 | |
| XX | 4-biphenyl | H | H | —CH₂CH₂CH₂-phenyl | B | 34.8 | |
| XXI | 2-CO₂Me-cyclohexyl | H | H | —CH₂CH₂CH₂-phenyl | B | 14.5 | |
| XXII | 4-CO₂Me-phenyl | H | H | —CH₂CH₂CH₂-phenyl | B | 11.4 | |

TABLE I-continued

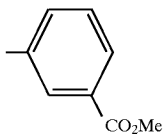

| Example No. | A | R⁴ | R² | R¹ | Method | Yield (% of theory) | $R_f$* |
|---|---|---|---|---|---|---|---|
| XXIII | 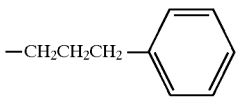 | H | H | —CH₂CH₂CH₂— 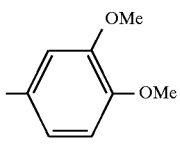 | B | 28.7 | |
| XXIV | 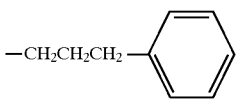 | H | H | —CH₂CH₂CH₂— 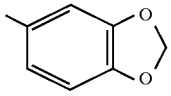 | B | 11.7 | |
| XXV | 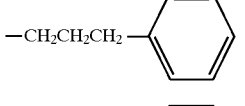 | H | H | —CH₂CH₂CH₂— 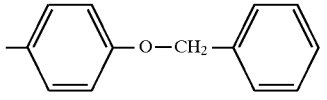 | B | | |
| XXVI | 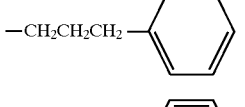 | H | H | —CH₂CH₂CH₂— 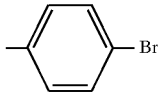 | B | | |
| XXVII | 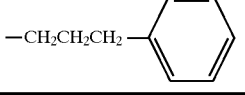 | H | H | —CH₂CH₂CH₂— | B | 45 | 0.41 |

*Mobile phase: CH₂Cl₂/MeOH 10:1

Preparation Examples

General working instructions for synthesis of the 2,9-disubstituted purin-6-ones (Formula I)

Method A:

1 mmol of 1-substituted 5-acylamnino-irnidazole-4carboxamide and 5 mmol of potassium carbonate are boiled under reflux overnight in 20 ml of ethanol and 10 ml of water. The solvent is evaporated in vacuo, the residue is taken up in 20 ml of ethyl acetate and the mixture is extracted by shaking with satutted NaCl solution. The organic phase is separated off, dried over Na₂SO₄ and evaporated in vacuo. The residue is purified by recrystallization or flash chromnatography.

Method B: (analogous to EP 0526 004)

1 mmol of 1-substituted 5-acylamino-imidazole4-carboxarnide, 5 mmol of potassium carbonate and 1 ml of 30% H₂O₂ solution are boiled under reflux overnight in 10 ml of water and 10 ml of ethanol (monitoring by TLC). Further working up is carried out analogously to instructions A.

The 2,9-disubstituted purin-6-ones listed in Table 1 are prepared in accordance with these two instructions:

TABLE 1

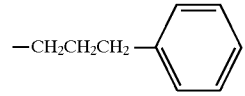

| Example No. | A | R⁴ | R² | R¹ | Method | Yield (% of theory) | Melting point (°C.)/R_f |
|---|---|---|---|---|---|---|---|
| 1 | —CH₃ | CH₃ | OH | n-hexyl | A | 68.6 | 0.39 (CH₂Cl₂/CH₃OH 10:1) |
| 2 | —C(CH₃)₃ | CH₃ | OH | n-hexyl | A | 49.1 | 237 (ethyl acetate/diethyl ether) |
| 3 | -n-C₁₇H₃₅ | CH₃ | OH | n-hexyl | B | 24.8 | 0.52 (CH₂Cl₂/CH₃OH 10:1) |
| 4 | —C₆H₅ | CH₃ | OH | n-hexyl | A | 48.9 | 249 (ethyl acetate/diethyl ether) |
| 5 | -4-Cl—C₆H₄ | CH₃ | OH | n-hexyl | A | 27.9 | 235 (C₂H₅OH/ether) |
| 6 | —C₆H₁₁ | CH₃ | OH | n-hexyl | B | 72.9 | 166 (ethyl acetate/diethyl ether) |
| 7 | —C₆H₁₁ | CH₃ | H | n-hexyl | A | 42.1 | 154 (ethyl acetate/diethyl ether) |
| 8 | —C₆H₁₁ | CH₃ | OH | —CH₂CH₂CH₂—C₆H₅ | B | 43.5 | 0.44 (CH₂Cl₂/CH₃OH 10:1) |
| 9 | 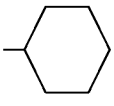 | H | H | —CH₂CH₂CH₂—C₆H₅ | A | 44.9 | 162° C. |
| 10 | 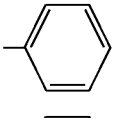 | H | H | —CH₂CH₂CH₂—C₆H₅ | A | 40.3 | 212° C. |
| 11 | 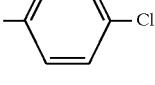 | H | H | —CH₂CH₂CH₂—C₆H₅ | A | 34.2 | 184° C. |
| 12 | 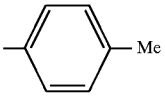 | H | H | —CH₂CH₂CH₂—C₆H₅ | A | 49.8 | 179° C. |
| 13 | 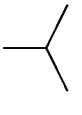 | H | H | —CH₂CH₂CH₂—C₆H₅ | A | 38.9 | 0.38 |
| 14 |  | H | H | —CH₂CH₂CH₂—C₆H₅ | A | 44.1 | 0.41 |
| 15 | 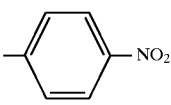 | H | H | —CH₂CH₂CH₂—C₆H₅ | A | 36 | 194° C. |
| 16 | 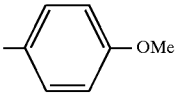 | H | H | —CH₂CH₂CH₂—C₆H₅ | A | 49.3 | 139° C. |
| 17 | 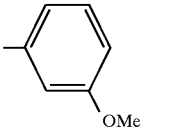 | H | H | —CH₂CH₂CH₂—C₆H₅ | A | 41.7 | 125° C. |

TABLE 1-continued
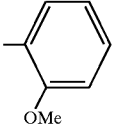
| Example No. | A | R⁴ | R² | R¹ | Method | Yield (% of theory) | Melting point (°C.)/$R_f$ |
|---|---|---|---|---|---|---|---|
| 18 | 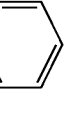 | H | H | —CH₂CH₂CH₂—  | A | | |
| 19 |  | H | H | —CH₂CH₂CH₂— 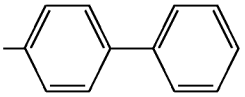 | A | 48.9 | 149° C. |
| 20 |  | H | H | —CH₂CH₂CH₂— 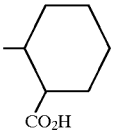 | A | 32.5 | 164° C. |
| 21 | 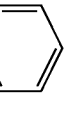 | H | H | —CH₂CH₂CH₂— 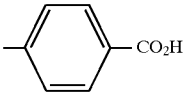 | A | 35.1 | 128° C. |
| 22 | 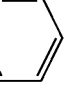 | H | H | —CH₂CH₂CH₂— 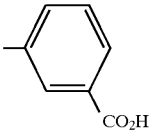 | A | 29.2 | 235° C. (decomposition) |
| 23 | 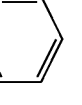 | H | H | —CH₂CH₂CH₂— 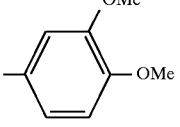 | A | 44.6 | 243° C. (decomposition) |
| 24 | 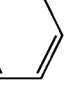 | H | H | —CH₂CH₂CH₂— 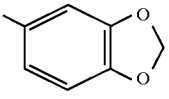 | A | 37.1 | 195° C. |
| 25 | 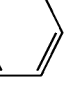 | H | H | —CH₂CH₂CH₂— 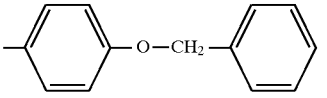 | A | 42.6 | 182° C. |
| 26 | 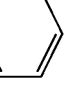 | H | H | —CH₂CH₂CH₂— 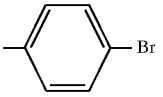 | A | 41.1 | 245° C. |
| 27 | 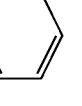 | H | H | —CH₂CH₂CH₂— | A | 32.7 | 190° C. |

TABLE 1-continued

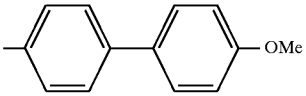

| Example No. | A | R⁴ | R² | R¹ | Method | Yield (% of theory) | Melting point (°C.)/R_f |
|---|---|---|---|---|---|---|---|
| 28 |  —OMe | H | H | —CH₂CH₂CH₂— (phenyl) | A | 35 | 152° C. |

Example 29

9-(2-Methanesulphonyloxy-3-nonyl)-2-cyclohexyl-purin-6-one

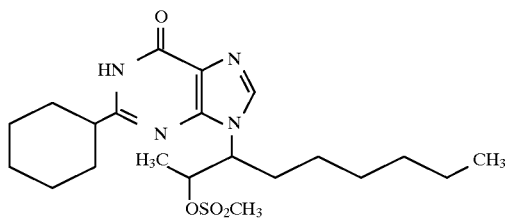

0.36 g (1 mmol) of 9-(2-hydroxy-3-nonyl)-2-cyclohexyl-purin-6-one (Example 6) and 0.3 ml of triethylamine are stirred in 5 rnl of absolute $CH_2Cl_2$ at 0° C. 0.1 ml of methanesulphonyl chloride, dissolved in 2.5 ml of absolute $CH_2Cl_2$ is then added dropwise. After 30 minutes at 0° C., the mixture is extracted by shaking with 10 ml of saturated $NaHCO_3$ solution, 10 ml of 2 N HCl solution and 10 ml of saturated $NaHCO_3$ solution. The organic phase is dried over $Na_2SO_4$, the solvent is evaporated in vacuo and the residue is purified by flash chromatograhy using ethyl acetate/ $CH_2Cl_2/CH_3OH$ 10:1 as the eluent.
Yield: 0.198 g (45.2%)
$R_f$=0.52 ($CH_2Cl_2/CH_3OH$ 10:1)

Example 30

9-(2-Methanesulphonyl-6-phenyl-3-hexyl)-2-cyclohexyl-purin-6one

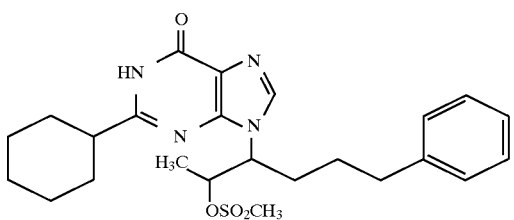

The title compound is prepared analogously to the instructions of Example 29 starting from 9-(2-hydroxy-6phenyl-3-hexyl)-2-cyclohexyl-purin-6one (Example 8).
Yield: 89.7%
$R_f$=0.5 ($CH_2Cl/CH_3OH$ 10:1)

Example 31

9-(2-Azido-3-nonyl)-2-cyclohexyl-purin-6-one

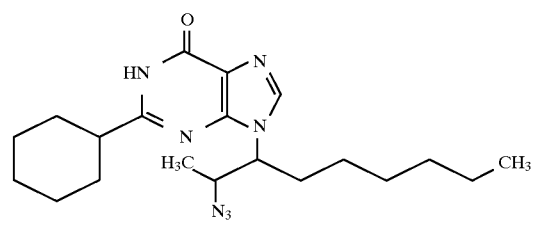

0.381 g (0.87 mmol) of 9-(2-methanesulphonyloxy-3-nonyl)-2-cyclohexyl-purin-6-one (Example 29) and 0.113 g (1.74 mmol) of sodium azide are stirred in 5 ml of absolute DMF at 100° C. overnight. The mixture is cooled to 20° C., 30 ml of ethyl acetate are added and the mixture is washed twice with 50 ml of water each time and once with 50 ml of saturated NaCl solution. After drying over $Na_2SO_4$, the solvent is evaporated in vacuo and the residue is purified by flash chromatography (eluent: $CH_2Cl_2/CH_3OH$ 30:1).
$R_f$=0.55 ($CH_2C_2/CH_3OH$ 10:1)
Yield: 0.311 g (92.8%)

Example 32

9-(2-Azido-6-phenyl-3-hexyl)-2-cyclohexyl-purin-6-one

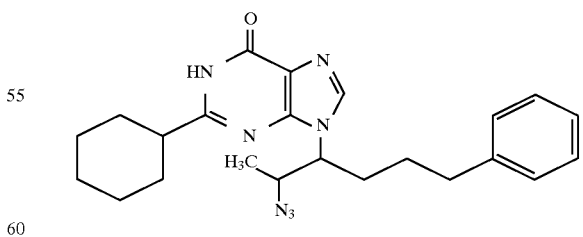

The title compound is prepared analogously to the instructions of Example 31 starting from 9-(2-methanesulphonyloxy-6-phenyl-3-hexyl)-2-cyclohexyl-purin-6-one (Example 30).
Yield: 0.372 g (78.2%)
$R_f$=0.54 ($CH_2Cl_2/CH_3OH$ 10:1)

Example 33

9-(2-Oxo-3-nonyl)-2-cyclohexyl-purin-6-one

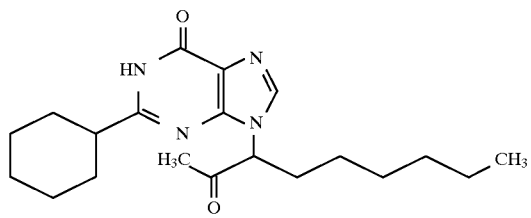

0.2 ml of absolute DMSO in 3 ml of absolute CH$_2$Cl$_2$ is added dropwise to 0.15 ml of oxalyl chloride in 5 ml of absolute CH$_2$Cl$_2$ at −60° C. and the mixture is subsequently stirred at -60° C for 20 minutes. 540 mg (1.5 mmol) of 9-(2-hydroxy-3-nonyl)-2-cyclohexyl-purin-6-one (Example 6) in 3 ml of CH$_2$Cl$_2$ are then slowly added dropwise and the mixture is subsequently stirred at −60° C., for 1 hour. 1 ml of triethylamine in 3 ml of CH$_2$Cl$_2$ is added dropwise to this solution. The mixture is allowed to come to room temperature, 7 ml of water are added and the organic phase is separated off. The organic phase is washed with 10 ml of 2 N HCl and 10 ml of saturated NaCl solution, dried over Na$_2$SO$_4$ and evaporated in vacuo. The residue is purified by flash chromatography (eluent: CH$_2$Cl$_2$/CH$_3$OH 40:1).

Yield: 0.416 g (77.4%)
R$_f$=0.47 (CH$_2$Cl$_2$/CH$_3$OH 10:1)

Exampe 34

9-(2-Oxo-6-phenyl-3-hexyl)2-cyclohexyl-purin-6-one

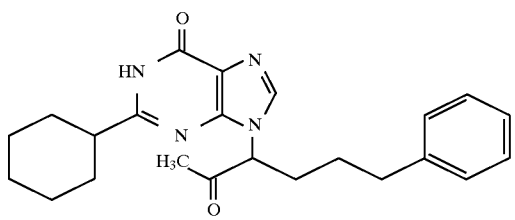

The title compound is prepared analogously to the instructions of Example 33 staring from 9-(2-hydroxy-6phenyl-3-nonyl)2-cyclohexyl-purin-6one (Example 8).

R$_f$=0.48 (CH$_2$Cl$_2$/CH$_3$OH 10:1)
Yield: 48.8%

We claim:

1. 2,9-disubstituted purin-6-one compounds of the formula (I):

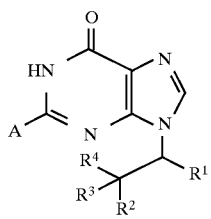

(I)

in which
R$^1$ represents hexyl, or phenylpropyl, wherein the phenyl group is optionally substituted by halogen, nitro, cyano, or straight-chain or branched alkyl having 1 to 6 carbon atoms;
R$^2$ represents hydrogen, hydroxyl, azido, straight-chain or branched alkyl having 1 to 6 carbon atoms, or a group of the formula —O—SO$_2$R$^5$;

wherein
R$^5$ represents straight-chain or branched aLkyl having 1 to 4 carbon atoms, or phenyl;
R$^3$ represents hydrogen, or
R$^2$ and R$^3$ together form a radical of the formula =O;
R$^4$ represents hydrogen, or straight-chain or branched alkyl having 1 to 4 carbon atoms;
A represents a radical of the formula

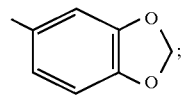

or represents cycloalkyl having 3 to 7 carbon atoms; or represents phenyl, which cycloalkyl or phenyl are optionally substituted 1 or 2 times by identical or different substituents selected from the group consisting of:
a) halogen,
b) trifluoromethyl,
c) carboxyl,
d) nitro,
e) cyano,
f) straight-chain or branched alkyl, alkoxycarbonyl or alkoxy, each of which has up to 5 carbon atoms and is optionally substituted by phenyl; and
g) phenyL which is optionally substituted by straight-chain or branched alkoxy having 1 to 5 carbon atoms;
and tautomers and salts thereof.

2. A method of treating impotence in a patient in need thereof which comprises administering to said patient an amount effective therefor of the compound or a tautomer or salt thereof according to claim 1.

3. A pharmaceutical composition comprising the compound or tautomer or salt thereof according to claim 1 and a pharmaceutically acceptable extender.

4. 2,9-disubstituted purin-6-ones according to claim 1, wherein such compound is 9-(5-phenyl-2-pentyl)-2-(4-methylphenyl)-purin-6-one of the formula

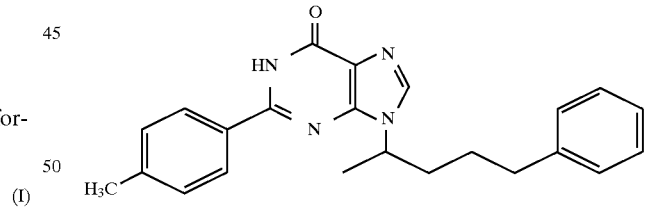

and tautomers and salts thereof.

5. 2,9-disubstituted purin-6-ones according to claim 1 wherein such compound is 9-(5-phenyl-2-pentyl)-2-(4-methoxyphenyl)-putin-6-one of the formula

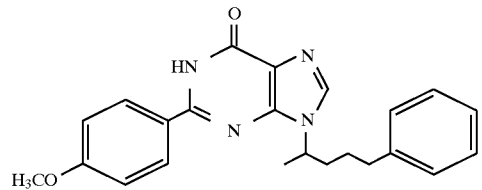

and tautomers and salts thereof.

6. 2,9-disubstituted purin-6-ones according to claim 1 wherein such compound is 9-(5-phenyl-2-pentyl)-2-(3-methoxyphenyl)-purin-6-one) of the formula

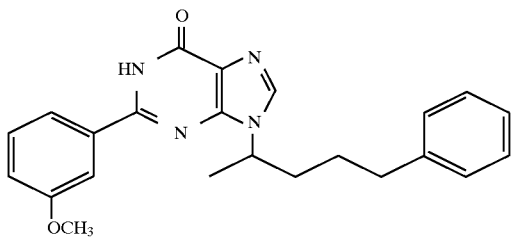

and tautomers and salts thereof.

7. 2,9-disubstituted purin-6-ones according to claim 1 wherein such compound is 9-(5-phenyl-2-pentyl)-2(phenyl)-purin-6-one of the formula

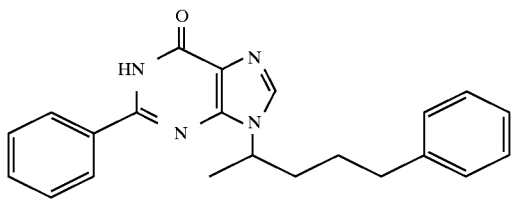

and tautomers and salts thereof.

8. 2,9-disubstituted purin-6-ones according to claim 1 wherein such compound is 9-(5-phenyl-2-pentyl)-2-(4-biphenyl)-purin-6-one of the formula

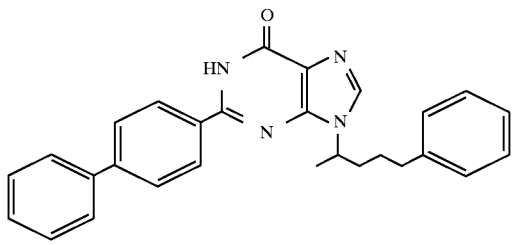

and tautomers and salts thereof.

9. 2,9-disubstituted purin-6-ones according to claim 1 wherein such compound is 9-(5-phenyl-2-pentyl)-2-(2-carboxycyclohexyl)-purin-6-one of the formula

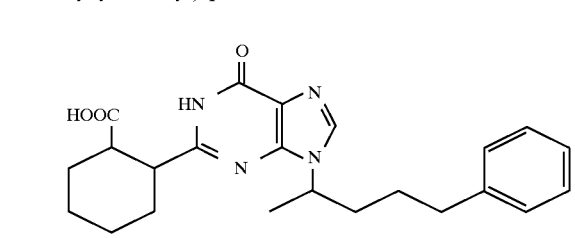

and tautomers and salts thereof.

10. 2,9-disubstituted purin-6-ones according to claim 1 wherein such compound is 9-(5-Phenyl-2-pentyl)-2-(3,4-methylendioxyphenyl)-purin-6-one of the formula

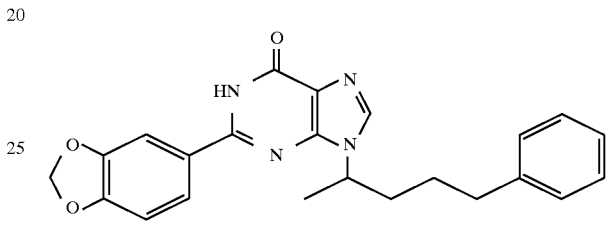

and tautomers and salts thereof.

11. 2,9-disubstituted purin-6-ones according to claim 1 wherein such compound is 9-(5-phenyl-2-pentyl)-2-(4-benzyloxypenyl)-purin-6-one of the formula

and tautomers and salts thereof.

12. 2,9-disubstituted purin-6-ones according to claim 1 wherein such compound is 9-(5-phenyl-2-pentyl)-2-(4-methoxybiphenyl)-purin-6-one of the formula

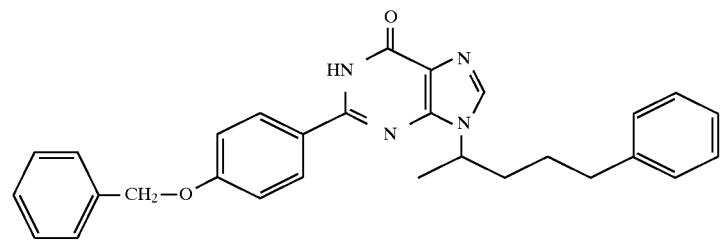

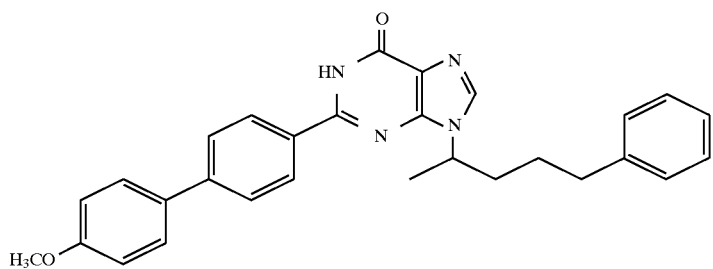
and tautomers and salts thereof.